US008781307B2

(12) United States Patent
Buzzetti (10) Patent No.: US 8,781,307 B2
(45) Date of Patent: Jul. 15, 2014

(54) VARIABLE VOLTAGE PORTABLE VAPORIZER

(76) Inventor: Michael Buzzetti, Paso Robles, CA (US)

(*) Notice: Subject to any disclaimer, the term of this patent is extended or adjusted under 35 U.S.C. 154(b) by 708 days.

(21) Appl. No.: 12/985,988

(22) Filed: Jan. 6, 2011

(65) Prior Publication Data

US 2011/0097060 A1 Apr. 28, 2011

Related U.S. Application Data (60) Provisional application No. 61/373,937, filed on Aug. 16, 2010.

(51) Int. Cl.
*F24F 6/08* (2006.01)
*A61M 11/04* (2006.01)
*F22B 1/28* (2006.01)

(52) U.S. Cl.
CPC ............ *F22B 1/28* (2013.01); *A61M 2205/583* (2013.01); *A61M 2205/8206* (2013.01); *A61M 11/044* (2013.01); *A61M 2205/8212* (2013.01); *A61M 11/041* (2013.01)
USPC .......................................... 392/395; 392/386

(58) Field of Classification Search
None
See application file for complete search history.

(56) References Cited

U.S. PATENT DOCUMENTS

| 2,324,359 | A | * | 7/1943 | Callan | 446/24 |
|---|---|---|---|---|---|
| 4,672,300 | A | * | 6/1987 | Harper | 323/222 |
| 4,764,660 | A | * | 8/1988 | Swiatosz | 392/397 |
| 4,818,843 | A | * | 4/1989 | Swiatosz | 392/397 |
| 4,877,989 | A | | 10/1989 | Drews et al. | |
| 4,899,269 | A | * | 2/1990 | Rouzies | 363/41 |
| 4,947,874 | A | * | 8/1990 | Brooks et al. | 131/329 |
| 5,060,671 | A | * | 10/1991 | Counts et al. | 131/329 |
| 5,095,921 | A | * | 3/1992 | Losee et al. | 131/194 |
| 5,261,424 | A | * | 11/1993 | Sprinkel, Jr. | 131/329 |
| 5,448,142 | A | * | 9/1995 | Severson et al. | 318/280 |
| 5,479,948 | A | * | 1/1996 | Counts et al. | 131/194 |
| 5,730,158 | A | * | 3/1998 | Collins et al. | 131/194 |
| 5,950,619 | A | | 9/1999 | van der Linden et al. | |
| 7,323,207 | B2 | * | 1/2008 | Nichols et al. | 427/1 |
| D581,520 | S | | 11/2008 | Williams et al. | |
| D603,033 | S | | 10/2009 | Kelnhofer | |

(Continued)

FOREIGN PATENT DOCUMENTS

KR 1020100008811 A 1/2010
KR 1020100080308 A 7/2010

OTHER PUBLICATIONS www.e-cigarette-forum.com, Michael Buzzetti, Forum Blog,Date of publication Apr. 17, 2010. Blog entry is that of the instant inventor. Not admitted as prior art. Downloaded from the internet on Jan. 6, 2011.
"Nuck FistPack v3.wmv," http://www.youtube.com/watch?v=TaLenHRrEO0, print out of opening screen shot and transcription of video, uploaded on Apr. 3, 2010.

(Continued)

*Primary Examiner* — Thor Campbell
(74) *Attorney, Agent, or Firm* — Daniel R. Kimbell; Karish & Bjorgum PC (57) ABSTRACT

A portable vaporizer having an electronic control unit electrically coupled to a power source and an atomizer. The electronic control unit utilizes a voltage regulator which allows changes in an output voltage supplied to the atomizer in response to a change in electrical resistance of a potentiometer incorporated therewith.

19 Claims, 3 Drawing Sheets

(56) References Cited

U.S. PATENT DOCUMENTS

| | | | |
|---|---|---|---|
| 2006/0193611 A1 | 8/2006 | Ruiz Ballesteros et al. | |
| 2008/0023003 A1 | 1/2008 | Rosenthal | |
| 2008/0230052 A1* | 9/2008 | Montaser | 128/200.16 |
| 2009/0041442 A1 | 2/2009 | Rouse, Jr. | |
| 2009/0283103 A1* | 11/2009 | Nielsen et al. | 131/273 |
| 2009/0293888 A1 | 12/2009 | Williams et al. | |
| 2010/0272421 A1* | 10/2010 | Liu et al. | 392/403 |
| 2011/0011396 A1* | 1/2011 | Fang | 128/202.21 |
| 2012/0230659 A1* | 9/2012 | Goodman et al. | 392/395 |
| 2013/0199528 A1* | 8/2013 | Goodman et al. | 128/203.26 |

OTHER PUBLICATIONS

"E-cig Box Mod—The fistpac V3 first look," http://www.youtube.com/watch?v=lvB2Gni6Ogk, print out of opening screen shot and transcription of video, uploaded on Apr. 23, 2010.

"FistPack e-cig Mod Review," http://www.youtube.com/watch?v=Prn31YY2uBs, print out of opening screen shot and transcription of video, uploaded on Jun. 1, 2010.

"Nuck'S Fist Pack Review," http://www.youtube.com/watch?v=Ae95TYaD26o, print out of opening screen shot and transcription of video, uploaded on Jun. 11, 2010.

* cited by examiner

VARIABLE VOLTAGE PORTABLE VAPORIZER

CROSS-REFERENCE TO RELATED APPLICATIONS

This application is a non-provisional application which takes benefit and priority under 35 U.S.C. §119(e) from U.S. provisional application Ser. No. 61/373,937 filed, Aug. 16, 2010 to the instant inventor. The aforementioned provisional patent application is hereby incorporated by reference as if fully set forth herein.

FEDERALLY SPONSORED RESEARCH AND DEVELOPMENT

Not Applicable

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

RELEVANT FIELD

This application is directed generally toward a portable vaporizer and more specifically toward a portable vaporizer having an adjustable voltage output.

BACKGROUND

Electronic cigarettes (E-Cigs) have been developed as an essentially smokeless alternative that provides smokers with the equivalent satisfaction of traditional smoking without many of the public health issues caused by secondary smoke exposure. Many of the E-Cigs known in the relevant art are adapted for portable use and utilize batteries to power an atomizer. Atomizers are available which utilize a number of different properties to cause atomization of a liquid including heating, piezometric vibration and ultrasonic vibration. However, all atomizers utilized by portable vaporizers require electrical power drawn from batteries in a generally uncontrolled manner. For example, a simple portable vaporizer can be constructed from as few as three parts; a battery, an atomizer and a switch to turn power supplied to the atomizer on and off. This simple arrangement works for short periods of time since the full output of the battery is applied continuously to the atomizer. Prolonged application of the full battery output can result in damage to either or both the battery and/or atomizer. At the very least, battery life is dramatically shortened to the point where a user is either limited to a few uses of the portable vaporizer before battery charging and/or replacement is required.

SUMMARY

In view of the foregoing, various exemplary embodiments of a variable voltage portable vaporizer are described herein. In one exemplary embodiment, a variable voltage portable vaporizer is constructed using low cost surface mount electronic components installed on a printed circuit board. An atomizer associated with the variable voltage portable vaporizer may receive a solution containing water, propylene glycol, nicotine, and a scent that emulates tobacco and/or other constituents in an atomizer. Power is supplied to the atomizer from a power source, usually one or more batteries. Application of power to the atomizer causes the received solution to vaporize. The vapors are then inhaled by a user. Application of power to the atomizer is controlled using a voltage regulator coupled with a potentiometer or switched resistor bank. The voltage regulator allows the user to adjust the variable voltage portable vaporizer to output a vapor concentration preferred by the user. In addition, the voltage regulator also controls the amount of power consumed by the atomizer, thus extending battery life. The type of voltage regulator used is not critical, thus, either buck-boost or a linear voltage regulator may be used.

For purposes of this specification, the term "pin" refers to an electrical connection made directly or indirectly with an electrical component. The term "tap" is used synonymously with the term "pin."

In an exemplary embodiment, a variable voltage portable vaporizer includes a main body having a proximal end and a distal end. An atomizer may be coupled with the proximal end of the main body. The atomizer typically includes an electrical heating element and a wick encompassing at least a portion of the electrical heating element. The wick is used to maintain the solution to be vaporized by the heating element. A power source is provided and is electrically coupled with an electronic control unit.

The power source may be contained within the main body intermediate the proximal and distal ends thereof. The electronic control unit may be electrically coupled with an electrical connector which supplies power to the atomizer and is dimensioned to fit within the main body intermediate the power source and the electrical heating element. In an exemplary embodiment, the electronic control unit includes a voltage regulator having a voltage input tap electrically coupled with the power source, a voltage output tap electrically coupled with the electrical heating element and a feedback voltage input tap. A variable electrical resistance means, typically a potentiometer, is electrically coupled with both the voltage output tap and feedback voltage input tap and configured such that a change in electrical resistance changes an output voltage in a range of about 3-6 volts supplied to an electrical connect in which the electrical heating element of the atomizer is connected. Typically, the voltage regulator is either a buck-boost type voltage regulator or a linear voltage type regulator.

In an exemplary embodiment, a power indication means is included to provide the user with a visual indication of when the power source is energizing the electronic control unit and hence the heating element of the atomizer.

In an exemplary embodiment, a low power indication means is included to provide the user with a visual indication of when the power source lacks sufficient capacity to energize the electrical heating element. A power switch is configured to energize the electronic control unit with the power source when closed. The power indication means and low power indication means are typically provided using a dual junction light emitting diode.

In an exemplary embodiment, the main body includes an elongated hollow tube which houses the electronic control unit and power source. The electronic control unit may be supported by an internal annular ring formed from internal discontinuities in wall thicknesses of the elongated hollow tube. In this exemplary embodiment, the electronic control unit may be axially aligned along a common longitudinal centerline with the main body and disposed upon the annular ring such that an outer circumference of the electronic control unit is in physical with a surface of the annular ring. The main body may be constructed from a metal which may be used to form a common electrical ground for the power source, electronic control unit and atomizer.

BRIEF DESCRIPTION OF DRAWINGS

The features and advantages of the various exemplary embodiments will become apparent from the following detailed description when considered in conjunction with the accompanying drawings. Where possible, the same reference numerals and characters are used to denote like features, elements, components or portions of the inventive embodiments. It is intended that changes and modifications can be made to the described exemplary embodiments without departing from the true scope and spirit of the inventive embodiments described herein and as is defined by the claims.

DETAILED DESCRIPTION

Various exemplary embodiments of a variable voltage portable vaporizer are disclosed herein. In the following detailed description, numerous specific details are set forth in order to provide a thorough understanding of the present inventive embodiments. It will be apparent, however, to one skilled in the art that the present inventive embodiments may be practiced without these specific details. In other instances, well-known structures, devices or components may be shown in block diagram form in order to avoid unnecessarily obscuring the present inventive embodiments.

In an exemplary embodiment, a variable voltage portable vaporizer is described herein. In one exemplary embodiment, a variable voltage portable vaporizer is constructed using low cost surface mount electronic components installed on a common printed circuit board. An atomizer associated with the variable voltage portable vaporizer is configured to receive, for example, a solution containing water, propylene glycol, nicotine, and a scent that emulates tobacco and/or other flavorings in an atomizer. Other constituents may be used in combination with or in lieu of the above listed vaporizing constituents. Power is supplied to the atomizer from a power source, usually by one or more batteries. Application of power to the atomizer causes the solution to vaporize. The vapors generated by the atomizer are then inhaled by a user. In order to prevent overheating of the atomizer and/or excess battery drain, an adjustable voltage regulator is provided. The voltage regulator allows the user to adjust the variable voltage portable vaporizer using a potentiometer or switched resistor bank to output a vapor concentration preferred by the user as well as controlling the amount of power consumed by the atomizer, thus extending battery life.

Referring to FIG. 1, an exemplary side view of a variable voltage portable vaporizer 100 is depicted. In this exemplary embodiment, the variable voltage portable vaporizer 100 includes a main body 5 having a proximal end 5a and a distal end 5b. An atomizer 15 is coupled with the proximal end 5a of the main body 5. The atomizer 15 may be coupled to the main body 5 with a proximal fitting 10. The proximal fitting 10 includes threads 105 complementary to those provided on an exterior surface or interior wall of the main body 5 (not shown.) Internal threads 105 are depicted in dotted lines. One skilled in the art will appreciate that the proximal and distal end fittings 10, 15 may be configured to engage threads provided an exterior surface of the main body 5.

A second set of raised threads 115 is provided along an axial centerline 40 of the main body 5 on a side opposite the proximal fitting threads 105. The second set of raised threads 115 are used to electrical and physically couple the proximal fitting 10 with the atomizer 15. The second set of raised threads 115 is complementary to internal threads (not shown) provided with the atomizer 15. When the second set of raised threads 115 is constructed from a metal material, an axial aperture is provided to allow an insulated electrical connection to supply power to a heating element 50 (FIG.1A) included in the atomizer 15. The atomizer 15 is primarily hollow and contains a small aperture 20 which allows air to be pulled through a wall of the atomizer 15 during inhalation of vapors by a user. The atomizer 15 is a common commercial product available from a number of vendors. For example, a suitable atomizer 15 is available from LiteSales USA, P.O. Box 651, Avis, Pa. 17721 or at URL http://www.litecig-usa.net. The atomizer 15 is depicted in the figures as having a cylindrical shape for exemplary purposes only. Other configurations are known in the relevant art and are readily adaptable to fit the second set of raised threads 115.

Figure 1A:
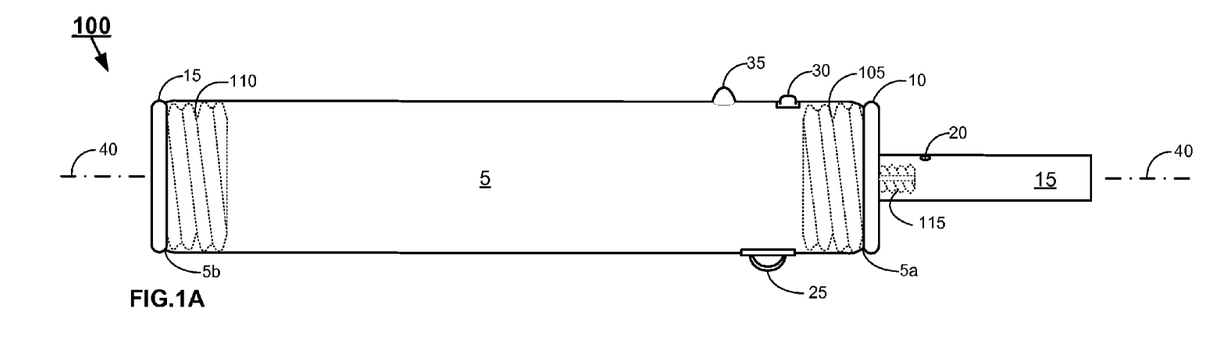
FIG. 1A—depicts a side view of a variable voltage portable vaporizer in accordance with an exemplary embodiment.

The main body 5 houses a set of user manipulative controls including a potentiometer 25, a power switch 30 and a power indicator light 35. In a preferred embodiment, the user controls 25, 30, 35 extend through one or more walls of the main body 5. The main body 5 may be constructed from any suitable material including various plastics and metals. For example, the main body 5 may be constructed from construction grade or aircraft grade aluminum (e.g., T6061) for light weight and strength. While the dimensions of the main body 5 are not critical, the variable voltage portable vaporizer 100 is intended to be used as a handheld device. In such implementations, the variable voltage portable vaporizer 100 should be longitudinally dimensioned to fit an average adult hand or approximately 10-15 cm in length with an outer diameter of 1-3 cm.

The distal end fitting 15 may likewise be provided with distal end threads 115 used to couple the distal end fitting 15 to the distal end 5b of the main body 5. As discussed above, the distal end threads 115 are complementary to those provided on an exterior surface or interior wall of the main body 5 (not shown.) In a preferred embodiment, both the proximal and distal fittings 10, 15 are constructed from a metal material having a diameter approximating that of the main body 5. Outer circumferential surfaces of the proximal and distal fittings 10, 15 may knurled (not shown) to allow for easy gripping.

The thicknesses of the proximal and distal fittings 10, 15 are not critical, although consideration should be given to the overall weight of the assembled variable voltage portable vaporizer 100. In an exemplary embodiment, assembly of the variable voltage portable vaporizer 100 is similar to that of a common flashlight where all components are aligned along a common longitudinal centerline 40 of the main body 5.

Figure 1B:
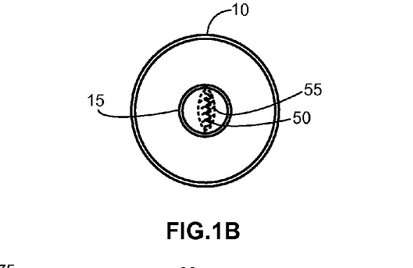
FIG. 1B—depicts a frontal end view of a variable voltage portable vaporizer in accordance with an exemplary embodiment.

Referring to FIG. 1B, an exemplary frontal end view of a variable voltage portable vaporizer 100 is depicted. In this exemplary embodiment, a top face of the proximal fitting 10 is shown with an end view of the atomizer 15 axially coupled thereto. As discussed above, the atomizer 15 is preferably aligned along a common longitudinal centerline 40 of the main body 5 which axially extends through the proximal fitting 10.

The atomizer 15 includes a heating element 50 and a wick 55 which encompasses at least a portion of the heating element 50. The wick 55 is used to maintain a solution to be vaporized by the heating element 50. The atomizer 15 is depicted in the figures as having a cylindrical shape for exemplary purposes only. Other configurations are known in the relevant art and are readily adaptable to fit the second set of threads 115.

In a preferred embodiment, one side of the heating element 50 is electrically insulated and the opposite side forms a common ground with the proximal fitting 10 and the main body 5. The atomizer 15 is essentially a hollow tube having an open end which allows a user to add a few drops of solution to be vaporized onto the wick 55 by the heating element 50. The opposite end of the atomizer 15 includes threads (not shown) complementary to the second set of raised threads 115 of the proximal fitting 10 and provides electrical continuity with the main body 5.

Figure 1C:
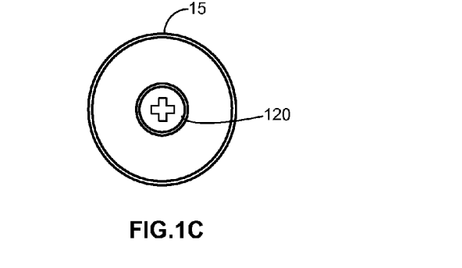
FIG. 1C—depicts a rear end view of a variable voltage portable vaporizer in accordance with an exemplary embodiment.

Referring to FIG. 1C, an exemplary rear end view of a variable voltage portable vaporizer 100 is depicted. In this exemplary embodiment, a top face of the distal fitting 15 is shown with a fastener 120 disposed along a common longitudinal centerline 40 of the main body 5. In this exemplary embodiment, the fastener 120 used to secure a spring contact 95 (FIG. 1D) in a proper alignment to ensure electrical continuity with the main body 5. The distal fitting 15 may be constructed from a metal material which provides electrical continuity with the spring contact 95 and the main body 5. A suitable metal material for both the proximal and distal fittings 10, 15 is aluminum or brass. One skilled in the art will appreciate that any suitable metal may be used as well. The fastener 120 is shown as having a Phillips head engagement profile for exemplary purposes only. One skilled in the art will appreciate that any commonly available engagement profile can be used.

Figure 1D:
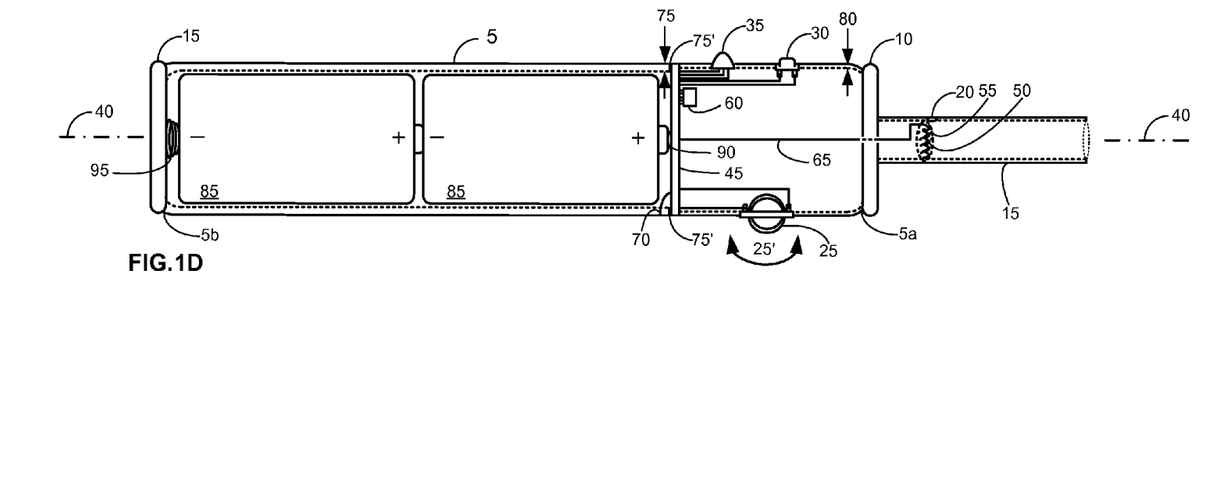
FIG. 1D—depicts a cross-sectional side view of a variable voltage portable vaporizer in accordance with an exemplary embodiment.

Referring to FIG. 1D, an exemplary cross-sectional side view of a variable voltage portable vaporizer 100 is depicted. In this exemplary embodiment, a layout of the internal components is shown in relative positions within the main body 5. The atomizer 15 includes a substantially hollow interior volume which allows a user to drip a solution for vaporization upon the wick 55 proximate or in contact with the heating element 50. In this exemplary embodiment, one side of the heating element 50 is grounded to the body of the atomizer 15. The body of the atomizer 15 is in electrical continuity with the proximal fitting 10 and main body 5 using the second set of raised threads 115.

The opposite side of the heating element 50 is electrically isolated from ground by a separate conductor 65. The conductor 65 is electrically connected to an electronic control unit 200, 300 (FIGS. 2,3) disposed on a printed circuit board 45.

The printed circuit board 45 may be constructed from composite epoxy material (CEM), polyimide or Teflon® and is primarily dependent on the operating conditions encountered within conduit 60. In most circumstances, CEM should be sufficient. The thickness of the printed circuit board 45 may be anywhere from about 0.5-2 mm again depending on the operating conditions in which variable voltage portable vaporizer 100 is expected to encounter.

The printed circuit board 45 is electrically connected to the potentiometer 25, the power switch 30 and the power indicator light 35. The potentiometer 25 may be of a rotating wheel type 25' or a linear slide type (not shown). The power switch 30 is of a normally open pushbutton type which maintains a closed circuit as long as the pushbutton remains depressed by a user. In an alternate exemplary embodiment, the power switch 30 may be of a normally open touch sensitive type which forms a closed circuit as long as the contact area is contacted by a user. The power indicator light 35 is a light emitting diode (LED) which visually indicates to the user when power is being supplied to the heating element 50. The power indicator light 35 may be a single junction type LED or a dual junction type LED.

In the single junction type, the LED 35 simply provides indication to the user when power is being supplied to the heating element 50, typically using a red colored light output. In the dual junction type, the LED 35 provides indication to the user when power is being supplied to the heating element 50 in a one color typically blue and also provides a low power indication in a separate color, for example red. The low power indication is visually displayed until a power source 85 has declined in output capacity insufficient to illuminate the LED 35 and power the heating element 50.

The printed circuit board 45 further includes a voltage regulator 60 installed thereupon. The voltage regulator 60 is in electrical continuity with the potentiometer 25, the power switch 30, the power indicator light 35, and other electronic components shown in FIGS. 2,3. In an exemplary embodiment, the printed circuit board 45 is electrically grounded to the main body 5 with an electrical conductor 70. In other exemplary embodiments where the main body 5 is constructed from non-conductive materials, the printed circuit board is electrically connected to a negative voltage side of the power source 85 using the electrical conductor 70. The potentiometer 25, the power switch 30, the power indicator light 35, voltage regulator 60 and other electronic components shown in FIGS. 2,3 form electronic control units 200, 300 which are described in the discussion accompanying FIGS. 2, 3 below.

In an exemplary embodiment, a positive voltage contact 90 is provided on a side of the printed circuit board 45 facing the distal fitting 15. The positive voltage contact 90 is positioned on the printed circuit board 45 so as to be axially aligned with the common longitudinal centerline 40 of the main body 5.

In an exemplary embodiment, the printed circuit board 45 is dimensioned to span a width of a defined portion of interior cross-section of the main body 5. The defined portion of the interior cross-section of the main body 5 is provided with an annular ring or lip 75' formed by circumferentially boring approximately a 1 mm thickness 75 from an interior wall 80 of the main body 5. The annular ring or lip 75' circumferentially supports the printed circuit board 45. Alternately, the annular ring or lip 75' may be formed by circumferentially compressing a discrete portion of the main body 5 (not shown) proximate to a position intended to be occupied by the printed circuit board 45.

In an exemplary embodiment, the power source 85 is contained within the main body 5 intermediate the proximal and distal ends 5a, 5b of the main body 5. In this exemplary embodiment, the power source 85 is comprised of a pair of cylindrical 3.7 VDC lithium ion batteries electrically connected in series and axially aligned with the common longitudinal centerline 40 of the main body 5. Electrical continuity with a positive terminal of the power source is provided by contact 90. Electrical continuity with a negative terminal of the power source is provided by spring contact 95. In an exemplary embodiment, the proximal fitting 10, distal fitting 15 and main body 5 are all constructed from electrically conductive materials. In this embodiment, the main body 5 forms a common negative ground in which all electrical components are grounded to. One skilled in the art will appreciate that batteries having different physical shapes and electrical characteristics may be used as well. In exemplary embodiments where any of the proximal fitting 10, distal fitting 15 and main body 5 is constructed from non-conductive materials, a separate negative ground conductor may provided from contact spring 95 to which all electrical components are then grounded to.

Figure 2:
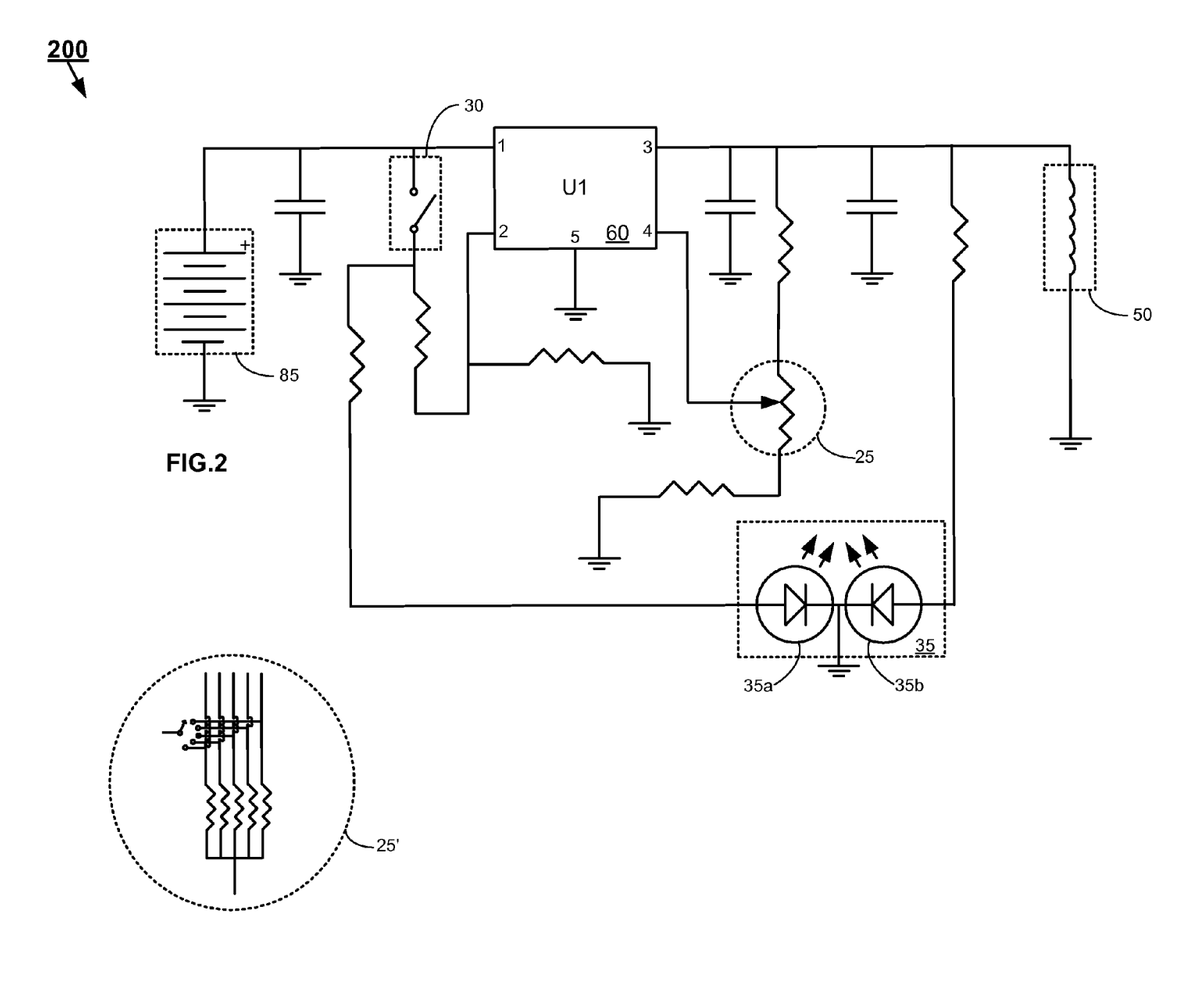
FIG. 2—depicts a first electrical circuit diagram of an electronic control unit for use in a variable voltage portable vaporizer in accordance with an exemplary embodiment.

Referring to FIG. 2, an exemplary first electrical circuit diagram of an electronic control unit 200 for use in a variable voltage portable vaporizer 100 is depicted. In this exemplary embodiment, the electronic control unit 200 utilizes a linear type voltage regulator U1 60. A suitable linear voltage regulator is available from Linear Technology, 1630 McCarthy Blvd, Milpitas, Calif. 95035, model LT1963A. Specifications for model LT1963A can be downloaded at URL http://www.linear.com.

The linear voltage regulator U1 60 requires resistors and capacitors which operate as part of a resistance/capacitance circuit. In an exemplary embodiment, the linear voltage regulator U1 60 receives a supply voltage of approximately +7.4 VDC at pin 1 from the power source 85. Upon closing of the power switch 30, the voltage regulator U1 60 outputs a regulated voltage at pin 3. The output voltage available at pin 3 may be adjusted to approximately in range of +6.0 VDC down to approximately +3.0 VDC by varying the resistance supplied by the potentiometer 25 connected to voltage feedback pin 4. One skilled in the art will appreciate that the potentiometer 25 may be substituted for a rotary or slide switch coupled to a switchable bank of fixed resistors having different resistances 25' to allow incremental adjustment of the output voltage supplied to the heating element 50.

The ability to vary the output voltage available to the heating element 50 allows a user to adjust the amount of heat generated by the heating element 50 and thus allowing adjustment of the amount of vaporization according to a user's personal preference. Allowing the full +6.0 VDC to be supplied to the heating element 50 will generate the greatest amount of vapor output while reducing the voltage to the minimum +3.0 VDC will generate the least amount of vapor output. The adjustment of the potentiometer 25 therefore requires balancing personal preferences with the battery life available from the power source 85.

The voltage output from pin 3 of voltage regulator U1 60 is provided to the heating element 50 so long as the power switch 30 remains closed. Closing of the power switch 30 also allows voltage to flow to the power indicator 35 (35*a*) which remains illuminated so long as the power switch 30 remains closed. In exemplary embodiments where a dual junction power indicator 35*a*, 35*b* LED is employed, voltage output from pin 3 allows voltage to flow to the second half of power indicator 35*b*. The second half of power indicator 35*b* remains illuminated so long as the power switch 30 remains closed and sufficient voltage is output from pin 3 of voltage regulator U1 60. Should the output voltage from pin 3 of voltage regulator U1 60 fall below that required to power the second half of power indicator 35*b*, the second half of power indicator 35*b* extinguishes, alerting the user that the power source 85 needs to be recharged or replaced. Alternately, failure of the second half of power indicator 35*b* may indicate a fault somewhere in the electronic control unit 200.

Figure 3:
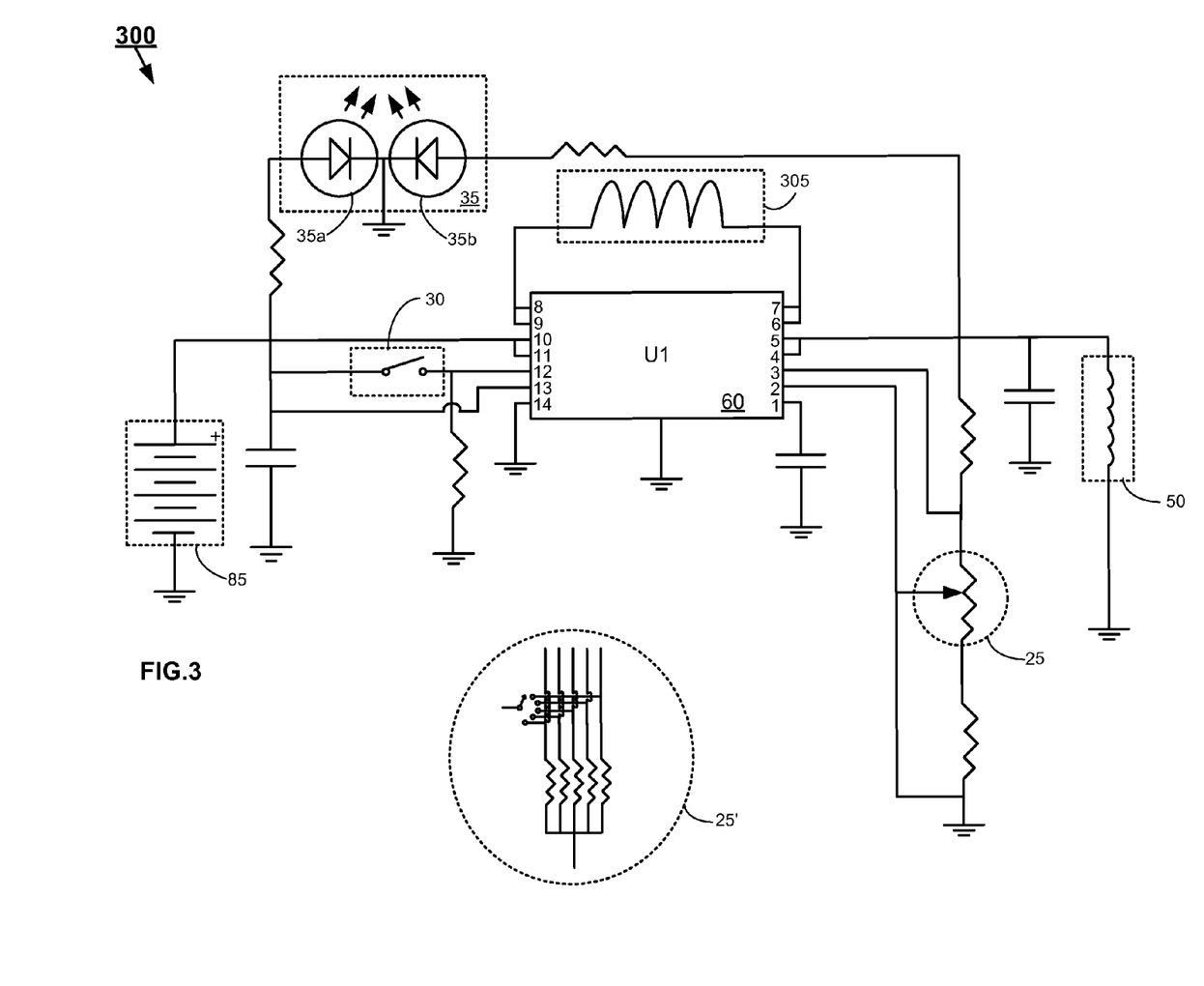
FIG. 3—depicts a second electrical circuit diagram of an electronic control unit for use in a variable voltage portable vaporizer in accordance with an exemplary embodiment.

Referring to FIG. 3, an exemplary second electrical circuit diagram of an electronic control unit 300 for use in a variable voltage portable vaporizer 100 is depicted. In this exemplary embodiment, the electronic control unit 300 utilizes a buck-boost type voltage regulator U1 60. A suitable buck-boost voltage regulator is available from Texas Instruments, Inc., 12500 TI Boulevard, Dallas, Tex. 75243 model TPS63020. Specifications for model TPS63020 can be downloaded at URL http://www.TI.com.

The buck-boost type voltage regulator U1 60 provides greater energy efficiency than is available from the simple linear type voltage regulator described in the discussion accompanying FIG. 2. The buck-boost type voltage regulator U1 60 requires an inductor 305 which operates as part of an inductance/capacitance circuit.

In this exemplary embodiment, the voltage regulator U1 60 receives a supply voltage of approximately +7.4 VDC at pin 10 from the power source 85. Upon closing of the power switch 30, the voltage regulator U1 60 outputs a regulated voltage at pin 5. The output voltage available at pin 5 may be adjusted as before in range of approximately +6.0 VDC down to approximately +3.0 VDC by varying the resistance supplied by the potentiometer 25 connected to voltage feedback pin 3. One skilled in the art will appreciate that the potentiometer 25 may be substituted for a rotary or slide switch coupled to a switchable bank of fixed resistors having different resistances 25' to allow incremental adjustment of the output voltage supplied to the heating element 50.

As discussed above, the ability to vary the output voltage available to the heating element 50 allows a user to adjust the amount of heat generated by the heating element 50 and thus allowing adjustment of the amount of vaporization according to a user's personal preference. Allowing the full +6.0 VDC to be supplied to the heating element 50 will generate the greatest amount of vapor output while reducing the voltage to the minimum +3.0 VDC will generate the least amount of vapor output. The adjustment of the potentiometer 25 therefore requires balancing personal preferences with battery life available from the power source 85.

The voltage output from pin 5 of voltage regulator U1 60 is provided to the heating element 50 so long as the power switch 30 remains closed. Closing of the power switch 30 also allows voltage to flow to the power indicator 35 (35*a*) which remains illuminated so long as the power switch 30 remains closed. In exemplary embodiments where a dual junction power indicator 35 (35*a*, 35*b*) LED is employed, voltage output from pin 5 allows voltage to flow to the second half of power indicator 35*b*.

As before, the second half of power indicator 35*b* remains illuminated so long as the power switch 30 remains closed and sufficient voltage is output from pin 5 of voltage regulator U1 60. Should the output voltage from pin 5 of voltage regulator U1 60 fall below that required to power the second half of power indicator 35*b*, the second half of power indicator 35*b* extinguishes, alerting the user that the power source 85 needs to be recharged or replaced. Alternately, failure of the second half of power indicator 35*b* may indicate a fault somewhere in the electronic control unit 200.

The various exemplary inventive embodiments described herein are intended to be merely illustrative of the principles underlying the inventive concept. It is therefore contemplated that various modifications of the disclosed embodiments will without departing from the inventive spirit and scope be apparent to persons of ordinary skill in the art. They are not intended to limit the various exemplary inventive embodiments to any precise form described. In particular, it is contemplated the variable voltage portable vaporizer 100 may utilize different electronic components, operating voltages and layouts than those described herein. No specific limitation is intended to executable instruction sequences described herein. Other variations and inventive embodiments are possible in light of the above teachings, and it is not intended that the inventive scope be limited by this specification, but rather by the Claims following herein.

What is claimed:

1. A portable vaporizer comprising:
a main body;
means for electrically coupling the main body with an atomizer;
an electronic control unit electrically coupled to the means and dimensioned to fit within the main body, the electronic control unit comprising:
a potentiometer electrically coupled with a voltage regulator for variably controlling an output voltage supplied to the means, wherein the voltage regulator is a buck-boost voltage regulator configured to change an output voltage in response to a change in electrical resistance of the potentiometer electrically coupled thereto, and;
a power source electrically coupled to the electronic control unit and disposed within the main body of the portable vaporizer.

2. The portable vaporizer of claim 1 further comprising:
a power switch configured to energize the electronic control unit with the power source when closed.

3. The portable vaporizer of claim 2 further comprising:
power indication means for providing a visual indication of when the power source is energizing the electronic control unit.

4. The portable vaporizer of claim 1 wherein the atomizer comprises:
an electrical heating element; and
a wick encompassing at least a portion of the electrical heating element.

5. The portable vaporizer of claim 3 wherein the power indication means comprises:
a light emitting diode electrically coupled with the electronic control unit.

6. The portable vaporizer of claim 1 wherein the power source generates an electrical potential of greater than 3 volts of direct current.

7. The portable vaporizer of claim 1 wherein the voltage regulator is a linear voltage regulator configured to change an output voltage in response to a change in electrical resistance of the potentiometer electrically coupled thereto.

8. The portable vaporizer of claim 1 wherein the electronic control unit is axially aligned along a common longitudinal centerline of the main body and disposed intermediate the power source and the means.

9. The portable vaporizer of claim 1, wherein the main body has a proximal end and a distal end, wherein the means for electrically coupling the main body with an atomizer couples the proximal end of the main body with the atomizer; and wherein the power source electrically coupled to the electronic control unit and disposed within the main body of the portable vaporizer is intermediate the proximal and distal ends thereof.

10. A portable vaporizer having a main body with an electronic control unit disposed therein, the electronic control unit comprising:
a voltage regulator having a voltage input tap, a voltage output tap and a voltage feedback tap;
the voltage input tap electrically being coupled with a power source, the voltage output tap being electrically coupled with a potentiometer and an atomizer tap, the voltage feedback tap being electrically coupled with the potentiometer; and
the voltage regulator configured such that a change in a feedback voltage supplied through the potentiometer changes an output voltage supplied to the atomizer tap.

11. The portable vaporizer of claim 10 wherein the voltage regulator is a buck-boost voltage regulator.

12. The portable vaporizer of claim 10 wherein the potentiometer is configured as user adjustable.

13. The portable vaporizer of claim 1 wherein the power source generates an electrical potential of greater than 3 volts of direct current.

14. A portable vaporizer comprising:
a main body of the portable vaporizer having a proximal end and a distal end and dimensioned to be held within a hand of a user;
means for coupling the proximal end of the main body with an atomizer;
a power source electrically coupled with an electronic control unit, the power source being disposed within the main body intermediate the proximal and distal ends thereof; and
the electronic control unit electrically coupled to the means, the electronic control unit being dimensioned to fit within the main body intermediate the power source and the means, the electronic control unit comprising:
a voltage regulator having a voltage input tap, a voltage output tap, and a feedback voltage tap; the voltage input tap being electrically coupled with the power source, the voltage output tap being electrically coupled with the means and the feedback voltage input tap;
a potentiometer electrically coupled with both the voltage output tap and feedback voltage input tap and configured such that a change in electrical resistance of the potentiometer changes an output voltage by 3-6 volts supplied to the means;
power indication means for providing a visual indication of when the power source is energizing the electronic control unit; and
low power indication means for providing a visual indication of when the power source lacks sufficient capacity to energize the means.

15. The portable vaporizer of claim 14 wherein the main body comprises:
an elongated hollow tube which houses the electronic control unit and power source, the electronic control unit being supported by an internal annular ring formed from internal discontinuities in wall thicknesses of the elongated hollow tube.

16. The portable vaporizer of claim 14 wherein the power indication means and low power indication means comprise a dual junction light emitting diode.

17. The portable vaporizer of claim 14 wherein the main body is constructed from a metal which forms a common electrical ground for the power source, electronic control unit and the means.

18. The portable vaporizer of claim 14 wherein the voltage regulator is selected from the group consisting of a buck-boost voltage regulator and a linear voltage regulator.

19. The portable vaporizer of claim 15 wherein the electronic control unit is axially aligned along a common longitudinal center with the main body and disposed upon the annular ring such that an outer circumference of the electronic control unit is in physical contact with a surface of the annular ring.

\* \* \* \* \*